United States Patent [19]

Zhirnov et al.

[11] Patent Number: 5,723,439
[45] Date of Patent: Mar. 3, 1998

[54] PHARMACEUTICAL AEROSOL COMPOSITION AND APPLICATION THEREOF FOR TREATMENT AND PROPHYLAXIS OF VIRAL DISEASES

[75] Inventors: Oleg Petrovich Zhirnov, Russian Federation, Moskovskaya Oblast, Dedovsk, ulitsa volokolamskaya, 60/12, kv. 15; Alexandr Valentinovich Ovcharenko, Dolgoprudny, both of Russian Federation

[73] Assignee: Oleg Petrovich Zhirnov, Russian Federation

[21] Appl. No.: 39,393

[22] PCT Filed: Aug. 19, 1992

[86] PCT No.: PCT/RU92/00164

§ 371 Date: Jun. 21, 1993

§ 102(e) Date: Jun. 21, 1993

[87] PCT Pub. No.: WO93/03708

PCT Pub. Date: Mar. 4, 1993

[30] Foreign Application Priority Data

Aug. 21, 1991 [RU] Russian Federation ............... 5000531

[51] Int. Cl.⁶ .................................................. A61K 38/00
[52] U.S. Cl. ........................................ 514/12; 514/957
[58] Field of Search ........................................ 514/12, 957

[56] References Cited

U.S. PATENT DOCUMENTS 4,153,687  5/1979  Schnabel et al. .................. 424/177
4,613,500  9/1986  Suzuki et al. ...................... 429/85
5,262,157  11/1993  Bernard et al. ................... 424/45

OTHER PUBLICATIONS

Gebhard, W. et al. "Biochemistry of Aprotinin . . . " Proteinase Inhibitors, Chapter 10, (1986) pp. 375–388.

Zhirnov, O.P. "High Protection . . . " Journal of Medical Virology 21, (1987) pp. 161–167.

Hubbard et al. PNAS, USA vol. 86 pp. 680–684 (1989).

R. Gordon Douglas, Jr. "Respiratory Diseases" Antiviral Agents and Viral Diseases of Man, Raven Press, New York, 1979, pp. 385–429.

Remington's Pharmaceutical Sciences, pp. 1694–1712, 1990.

*Primary Examiner*—Toni R. Scheiner
*Assistant Examiner*—Sheela J. Huff
*Attorney, Agent, or Firm*—Ladas & Parry

[57] ABSTRACT

The composition contains as the active substance an inhibitor of proteinases selected from the group of aprotinin, a derivative thereof, or an aprotinin-like substance in the form of an aqueous solution or solid micronized particles or a size in the range of from 0.5 to 20 μm. The aqueous solution contains the active substance in an amount of from 1500 to 10,000 KIU/ml.

The composition is proposed for application in treatment and prophylaxis of predominantly viral respiratory diseases.

2 Claims, 3 Drawing Sheets

PHARMACEUTICAL AEROSOL COMPOSITION AND APPLICATION THEREOF FOR TREATMENT AND PROPHYLAXIS OF VIRAL DISEASES

THE FIELD OF TECHNOLOGY

The present invention pertains to a new pharmaceutical aerosol composition and employment thereof for treatment and prevention of viral diseases.

DESCRIPTION OF PRIOR ART

At present, a number of therapeutic substances are known such as amantadine (Douglas, R. G.—Respiratory Diseases., 1979, pp. 413–425. In: "Antiviral Agents and Viral Diseases of Man", Raven Press, New York, G. Galasso, ed.), ribavirin (Douglas, R. G.—Ibidem, pp. 425–428), and biologically active polypeptides such as interferon (Scott et al., Brit. Med. J., 1982, v. 284, p. 1822) which are capable of inhibiting an infectious process induced by orthomyxo— (influenza viruses) and paramyxoviruses. Their therapeutic effect is due to the capacity to block reproduction of the above-mentioned viruses. Therapeutically, they are employed in different medicinal forms: tablets, capsules, solutions for injections, and aerosols, the latter being most preferable. This is explained by the fact that in viral-bacterial respiratory diseases the broncho-pulmonary epithelium is primarily affected, therefore the employment of the active substance through the respiratory tract in the form of micronized particles of no more than 200 μm in size will be most effective. The application of the aerosol form of medicinal substances of the amantadine series is known, however, the above-mentioned therapeutic substances are active only against influenza type A viruses but not against influenza type B viruses, paramyxoviruses, and many other viruses, that is, they show a selective therapeutic effect.

Attempts are known to have been made to create antiviral medicinal drugs based on aprotinins, inhibits of proteinases (Zhirnov, O. P.—J. Med. Virol., 1987, 21:p.161–167). Aprotinins are natural low molecular polypeptides inhibiting a wide range of proteinases. There are officinal aprotinin preparations: Gordox (Gedeon Richter), Contrycal (Germed), Trasylol (Bayer AG), Antagosan (Behring). The antiviral and therapeutic effect (inhibition of pulmonary pathology, prevention of animal deaths) was achieved by parenteral (intraperitoneal) inoculation of aprotinin. A sufficiently high dose of aprotinin preparation was from 10,000 to 15,000 kallikrein-inhibiting units (KIU) (animal/day). When inoculated parenterally, aprotinin polypeptides are absorbed into the blood channel where, binding with various blood proteins, they change their physico-chemical (charge, ionization degree, molecular weight, conformation structure) and functional characteristics. Such protein complexing may result in masking and inhibition of aprotinin activity and blocking of the passage of the complexes from the blood into the respiratory tract. As a result, the mechanism of the antiviral effect is transformed and the therapeutic effect is lowered.

BRIEF DISCLOSURE OF THE ESSENCE OF THE INVENTION

The main purpose of the invention was to develop a pharmaceutical aerosol composition of the basis of biologically active polypeptide in the form of an aqueous solution or solid microparticles which, in a lower effective therapeutic dose, would exert an enhanced antiviral and pathogenetic effect in therapy or prophylaxis in man and animals suffering from respiratory tract diseases.

This task is solved by the fact that the pharmaceutical aerosol composition of the invention contains, as the active substance, a proteinase inhibitor of the aprotinino group dissolved in water in amounts of from 1500 to 10,000 KIU/ml of solution.

It is expedient, for better stability of the aerosol and enhancement of its adsorption in the respiratory tracts, to include into the composition a surfactant, preferably Twin-80 or glycerol. The proposed composition is applied predominantly for different parts of the respiratory tract.

The aprotinin consisting of microparticles of aerosol with different humidity is prepared by atomization of an aqueous solution in an air stream or a propellent by means of an atomizer providing the obtainment of a proper size of the particles in relation to the localization site of the infectious process.

This task is also solved by the fact that the pharmaceutical aerosol composition, according to the invention, contains, as the active substance solid micronized particles of a proteinase inhibitor selected from the group consisting of aprotinin, a derivative thereof, and an aprotinin-like substance the average sizes of which range from 0.5 to 20 μm.

The dry powder or compressed powder aerosol of the composition according to the invention is obtained by means of powder inhalator, or an aerosol device with a dosage meter.

The powder aerosol with this particle size is characterized by high efficacy in treatment of viral diseases by administration into the respiratory tract. It is expedient to combine the powder aerosol composition with various pharmaceutically acceptable ingredients: a vehicle, a surfactant which stabilize the aerosol and enhance its efficacy by inhalations or applications into the respiratory tract. A pharmaceutical vehicle is conducive to enhanced adsorption of the active substance in certain parts of the respiratory tract and prolongation of the therapeutic effect of the active substance which results in decreasing of the doses for treatment and prophylaxis.

Various vegetable oils, (caster, mint, eucaliptus) as well as glycerol and non-ion detergents such as Twin-80 may be used surfactants. The said surfactants prevent aggregation and improve dispersion of particles in the aerosol composition, enhance the adsorption of the active substance on the respiratory tract epithelium and improve the therapeutic effect of aerosol. In the application of the powder composition, according to the invention, in an aerosol device with a dose meter it is used with a pharmaceutically acceptable liquefied gas propellent.

The aerosol composition may additionally contain other prophylactic and therapeutic preparations—synergists: pentamidine, bronchodilators, antibiotics.

The aerosol of micronized particles of the composition, according to the invention, exerts an enhanced therapeutic effect on man or animal when administered into the nasopharynx and respiratory tract.

The aerosol of aprotinin, a derivative thereof or an protinin-like substance exerts a stronger therapeutic and marked prophylactic effect when used in doses 100 times lower than those needed for parenteral injections. The highest efficacy of the aerosol was achieved by its action on the lungs and lower respiratory tract when the average size of micronized particles with within a range of from 0.5 to 4 μm. With an increase in the particle size to 20 μm the best effect of the aerosol was on the nasopharynx and upper respiratory tract. The enhanced therapeutic function of aprotinins, derivatives thereof and aprotinin-like substances is likely to be due to structural transformations of the active substance molecule and changes of the targets of the pathogenetic action of the active substance administered in the aerosol form into the respiratory tract as compared with parenteral injections of an aqueous solution.

The conformation and ionization of the aprotinin molecule are changed by transition into the aerosol form, especially at the phase boundary (air-particle).

The structural transformations induced by aerosolation, in all probability, lead to the appearance of new physiological mechanisms and qualitative enhancement of the therapeutic effect of aprotinin and aprotinin-like substances.

In our opinion, the application of aerosols of aprotinin, a derivative thereof, and an aprotinin-like substance is possible not only by inhalation but also by instillation on the microbe- or virus-affected areas of the body and mucous membranes such as skin integuments, mucous membranes of the eyes, nasopharynx, throat, and the gastro-intestinal tract.

LIST OF DRAWINGS

Below, variants of the embodiment of the proposed invention are presented with reference to the drawings which, according to the invention, present:

FIG. 1—a dispersion profile of aprotinin aerosol microparticles;

FIG. 2—the dynamics of body weight changes in mice infected with influenza virus and treated with aprotinin aerosol;

FIGS. 3a–3d—the protective effect of aprotinin aerosol in mice infected with A/Aichi/2/68 (a, c), Sendai/960 (b), and B/HK/72 (d) viruses.

DETAILED DESCRIPTION OF THE INVENTION

Figure 1:
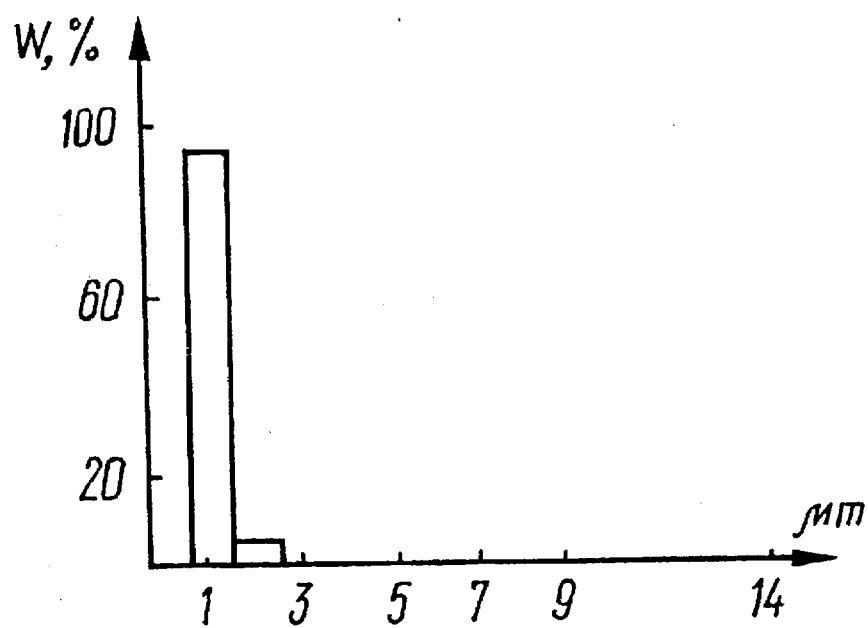

An aerosol composition has significant advantages over other medicinal forms for treatment and prevention of viral respiratory diseases. The aerosol composition, according to the present invention, contains, as the active substance, an inhibitor of proteinases selected from the group consisting of aprotinin, a derivative thereof, or an aprotinin-like substance which are biologically active polypeptides.

Aprotinins and aprotinin-like polypeptides may be obtained from organs of various animals as well as from snails, snake poisons, and from silkworm larvae. Aprotinin derivatives are obtained by modification of individual amino acids and covalent binding with different groupings. The resulting aprotinin derivatives retaining the main biological and anti-proteinase properties acquire higher stability and lack some side effects when used medicinally (Gerbhard, W. et al. "Proteinase Inhibitors". Elsevier Science Publishers, v. 10, p. 375–388, 1986).

Polypeptides are extracted and purified in an aqueous medium to achieve a pharmaceutically acceptable quality. To obtain aprotinin, a derivative thereof, or an aprotinin-like substance in the form of solid micronized particles, the aqueous solution of these purified polypeptides are subjected to lyophilization and comminution. The particle size is controlled by comminution pressure. An average size of the particles formed in the process is in a range of from 0.5 to 20 µm, predominantly from 0.5 to 10 µm. The particles of aprotinin, derivatives thereof and aprotinin-like particles of 0.5 to 4 µm in size ensure the transportation of the active substance to the middle and lower parts of the respiratory tract and those of 4 to 20 µm in size to the nasopharynx and upper respiratory tract.

Aqueous solutions of the said polypeptides and micronized solid particles thereof may be used for inhalations. It should be noted that, unlike other known polypeptides, for example, interferon, the polypeptides used in the invention are highly stable in the solid state and in aqueous solutions. They also retain their functional activity upon aerosolation which was determined by trypsin inhibition by aerosol.

At present, approved preparations of aprotinins are available such as Gordox (Gedeon Richter), Contrycal (Germed), Trastylol (Bayer AG), Antagosan (Behring) which may be used for aerosol preparation.

To prepare an aqueous solution of aprotinin we used Gordox, or Contrycal, Antagosan which was diluted in distilled water so as to contain from 1500 to 10,000 Kallikrein-inhibiting units (KIU) in 1 ml of the solution. These doses were established by experimental selection in serial dose-effect tests.

To increase the aerosol stability, it is proposed to introduce into the aqueous solution a surfactant, for instance, Twin-80, triton X-100 in amounts of from 0.01 to 5.0% weight of which are readily dissolved in water. These surfactants enlarge the active surface of aerosol particles of aprotinin, derivatives thereof or aprotinin-like substance owing to which their adsorption in the respiratory tract is improved and the protective effect of the aerosol increases. Additionally, the solution may contain glycerol as a surfactant in an amount of from 0.05 to 10 weight %.

A pneumatic system of the ejector type may be used for preparation of aerosol from the aqueous solution of the said polypeptides. The aqueous solution of the polypeptide is dispersed by evaporation of liquid fluorocarbon propellent or by forces of a high-speed gas stream, for instance, compressed air. Also, to make aerosol, an ultrasonic generator of Musson-I type (Trade Mark No. 25-2012.075-89, Altay Instrument-making Plant, Barnaul, Rossiya) may be used.

The aerosol cloud is formed by ultrasonic dispersion of the aqueous solution.

In the former instance, the resulting aerosol consisted predominantly of particles from 0.5 to 3.8 µm in size. Inhalation of such particles achieves and most adequate supply of aprotinin or aprotinin-like substances to the middle and low parts of the respiratory tract. It should be noted that under the pneumatic regimen, owing to rapid drying of the particles, the resulting aerosol cloud consists predominantly of dry particles (90%), the water concentration in the said aerosol being about 0.01 mg/ml.

Because of the lack of an air flow in the ultrasonic regimen there occurs partial condensation of the aerosol and the intensity of the particle drying is lower; the resulting aerosol cloud has the properties of a humid aerosol.

In the said aerosol, the particle size varied from 0.1 to 100 µm, predominantly from 3.5 to 7 µm, and upon inhalation it supplied the active substance to the nasopharynx and upper parts of the respiratory tract. This differentiation of aerosol supply permits a selection of one of the possible variants of preparation and use of the aerosol depending on the localization of an infectious focus. Positive therapeutic effects could be achieved by using both dry and humid types of aerosol, however, the dry aerosol was better tolerated.

Atomization of dry particles either through devices of the ejector type or through insufflators of the "Spinhaler" and "Rotahaler" types may be used for preparation of aerosol from solid micronized particles of aprotinin, derivatives thereof, or aprotinin-like substance. Another variant is the atomization of micronized particles from a suspension with a liquefied propellent.

In the first variant, particles of an active polypeptide may be used in combination with a carrier. The introduction of a carrier facilitates the preparation and standardization of the active substance powder and is conducive to its more effective supply to the upper parts of the respiratory tract (nasopharynx, pharynx, larynx, trachea). The carrier must be a non-toxic material chemically inert to the polypeptide used, not irritating for mucous membranes and acceptable for inhalation. Inorganic salts may be used as a carrier such as calcium carbonate, monosaccharides, for example, lactose, arabinose; polysaccharides such as dextrin, dextran. It is preferable to employ lactose in an amount 2–9 times by weight exceeding the active ingredient. The particle size in an aerosol, in particular, powder aerosol is the main control factor for their administration into the respiratory tract. Therefore the carrier particles must also be of certain size, in particular, not exceeding 200 µm. In larger size, the aerosol particles may irritate the respiratory tract tissues which is inadmissible. It is desirable for the carrier particles to be of from 30 to 80 µm in size.

In the second variant, dry micronized particles of aprotinin, derivative thereof or aprotinin-like substance are suspended in a liquefied gas aerosol propellent and applied as an aerosol in a hermetic vessel and a dosing device (valve). The liquefied propellent is a gas at room temperature (20° C.) and atmospheric pressure, that is, its boiling point must be below 20° C. at the atmospheric pressure. The liquid propellent must be non-toxic. Dimethyl ether, chlorides of lower alkyls, fluorinated or fluorochlorinated propellents of lower alkanes or mixtures thereof may be used as propellents. Such propellents are exemplified by dichlorofluoromethane ("propellent 12"), trichlorofluoromethane ("propellent 11"), monochlorodifluorometane ("Propellent 22"), 1,2-dichlorotetrafluoroethane ("propellent 114").

A compressed powder aerosol composition, according to the invention, may also contain a surfactant improving dissolution of the active substance in the propellent and subsequent formation of the aerosol particles and also enhancing the adsorption and alleviation the irritating effect of the aerosol on the respiratory epithelium.

A surfactant may be a liquid or a solid non-ionic surface-active substance. Preferably it would be a liquid surfactant selected from the group: glycerol, vegetable oils (mint, castor, eucaliptus), oleic or palmetic acids, used in an amount of up to 5 weight %. The mandatory condition for the use of a surfactant is its compatibility with the propellent. The higher the surfactant solubility in a propellent, the higher is its activity as a surface-active substance.

When the composition is in the form of a dry non-compressed powder, i.e. in capsules for inhalation, a single dose of a polypeptide used may vary from 0.01 to 20.0 mg, preferably from 0.05 to 0.5 mg.

When the composition is in the form of a compressed aerosol composition, it is desirable that the valve of the aerosol container provides for atomization of single doses of from 0.025 to 0.25 ml, preferably 0.05 to 0.1 ml.

Below are presented the examples of specific embodiment of the proposed invention.

EXAMPLE 1

Preparation of aerosol from an aqueous solution of aprotinin and calculation of single doses for mice An aqueous solution containing 1500–10,000 Kallikrein-inhibiting units (KIU) of aprotinin (Gordox) in 1 ml ($C_a$) was dispersed into a mouse incubation chamber by means of a pneumatic generator of the ejector type equipped with a system for compressed air supply. The aerosol from aqueous drops of aprotinin was formed by the forces of the compressed air stream. The velocity of the aerosol mixture supply into the chamber ($V_c$) was 9 liter/min, the intensity of dispersion of the aprotinin solution ($Q_a$) was 0.1 ml/min. The aprotinin concentration in the forming aerosol calculated by the formula $C_c = C_a \cdot Q_a / V_c$ was from 0.017 to 0.12 KIU/ml. The main part of the experiments with mice was carried out using an aerosol of a concentration of from 0.05 to 0.10 KIU/ml. The dose received by one mouse was calculated by the formula: Guyton=$C_c \cdot C_r \cdot P \cdot V \cdot t \cdot R$ (Guyton, A. C.—Am. J. Physiol., 947, v. 150, p. 70–77), wherein $C_c$—a relative cumulative concentration of aprotinin in the chamber in time t; P—mouse weight (6–10 g); V—specific respiratory volume of mouse (1.2 ml/g/min); R—coefficient of aerosol particles stay in the mouse respiratory tract (0.75). Since the speed of the forced air withdrawal from the chamber was equal to that of aerosol supply into the chamber, the coefficient $C_r$ was taken to be equal to 1. The results of the calculation yielded an average dose of aprotinin to be from 50 to 150 KIU/mouse/day (from 5 to 15 KIU per 1 g of mouse body weight per day). One KIU corresponds approximately to 0.35 TIU and 0.14 µg aprotinin protein.

To improve the aerosol stability in the atmosphere and enhance its adsorption on the respiratory epithelium, in some of the experiments surfactants were added to the solution: a non-ionic detergent (Twin-80 or Triton-X-100) and /or glycerol to final concentrations of from 0.05 to 10 vol. % and from 0.01 to 5.0 vol. %, respectively.

FIG. 1 shows the dispersion profile of aprotinin aerosol particles fed into the chamber. The diameter of the particles and their weight content in the aerosol was recorded by a laser controller Malvern-2200.

On the ordinate—relative weight content of particles of a given size in the aerosol, weight. %, on the abscissa—the category of the particles by size (µm): 1 (diameter from 0.5 to 3.8), 2 (3.8–6.5), 3 (6.5–8.5), 4 (8.5–10.5), 5 (10.5–13.0), 6 (13.0–16.7), 7 (16.7–25.0), 8 (25.1–35.0) 9 (35.1–42.0), 10 (42.1–53.5), 11 (53.5–90.5). It may be seen that 95% of the particles were up to 3.8 µm in size, 5% up to 6.5 µm. The particles of such size dried rapidly in the air stream, and the concentration of water in such aerosol approached the air humidity (about 0.01 mg/ml).

EXAMPLE 2

For the preparation of compressed powder aprotinin aerosol, either a dry powder manufactured by A WD Company (Germany) under the name of Contrycal, or a powder vacuum-lyophilized from the frozen aqueous aprotinin solution produced by Gedeon Richter and Behring Companies, were used. The powder was dispersed in an air-stream grinder, under different pressure varying from 5 to 120 psig followed by mixing of fractions of various degrees of dispersion to obtain a mixture of particles in the range of dimensions from 0.5 to 20 µm.

0.06 ml of eucaliptus oil were diluted in 6 ml of a mixture consisting of 3 parts by weight of "propellent 114" and 1 part by weight of "propellent 12", after which this solution was used for making a suspension of 50 mg of the said aprotinin powder, 250 mg of lactose with particle sizes ranging from 30 to 100 µm, and 0.05 ml Twin-80, the suspension was put into a 6 ml aluminium container with a valve calibrated for dispersion of a single dose of 0.05 ml. By pressing the valve, portions of aerosol were fed into the chamber where mice were incubated (8–18 feedings for an hour incubation). The dose of the aerosol was chosen to create in the chamber of aprotinin aerosol concentrations close to those in Example 1. For the maintenance of this concentration in the exposure chamber, aerosol was fed every 3–6 min.

The therapeutic and prophylactic effect of aprotinin aerosol prepared as described in Example 1 was studied in mice.

The mouse-pathogenic influenza A/Aichi/2/68 (H3N2) (orthomyxovirus), B/Hong Kong/72 viruses and paramyxovirus Sendai/960 were propagated in 9-day-old chick embryos. In studies of the chemotherapeutic and prophylactic effect of aprotinin aerosol, doses of virus were administered to mice in amounts ranging from the lethal dose for 50% of the mice to ($MLD_{50}$ dose) up to one hundred times this dose. The virus was administered either by intra nasal injections or inhalation of virus aerosol. As a result of the infections, the animals developed viral bronchopneumonia later complicated by microbial infections from the air (viral-bacterial pneumonia).

The experiments were carried out according to the following scheme:

Mice were infected with A/Aichi/2/68 or Sendai/960 virus in a dose of 50 $MLD_{50}$/mouse, or B/HK/72 virus in a dose of 1 $MLD_{50}$/mouse and then one group of the infected mice (20–30 animals per group) was exposed in a chamber to a gas-water mixture, and another in a chamber to the aprotinin aerosol for 30–60 min from 2 to 4 times daily. The pathological lesions in the lungs were evaluated on the 5th day postinfection, when the intensity of inflammation and virus titres in the lungs were close to the maximum. For this purpose, the lungs were removed from 2 mice of each groups and examined hestologically and visually. The control mice treated with inhalation of gas-water mixture without aprotinin exhibited total hemorrhagic inflammation which involved practically all (100%) the pneumonic tissue (viral-bacterial pneumonia). In the mice treated with aprotinin aerosol inhalations the intensity of inflammation was less marked and the hemorrhagic inflammation involved about 30 to 50% of the lung area. A similar pattern of lung involvement was observed in histological and macroscopic examinations of mice infected with Sendai/960 and B/HK/72 viruses and treated by a similar schedule with the aprotinin aerosol.

After intraperitoneal inoculation of the Gordox aprotinin preparation in a dose of 10.000 to 15.000 KIU/mouse/day, 5 to 6 injections daily for 6 days, to mice infected with 5 $MLD_{50}$ of A/Aichi/2/68 or Sendai/960 virus, the lung affection was much stronger involving 40%–60% of the lung area by visual evaluation. Thus, an aerosol dose of 50 to 150 KIU of aprotinin inhibited the development of lung pathology more effectively than did parenteral injections of 10.000 to 15.000 KIU of aprotinin solution.

Figure 2:
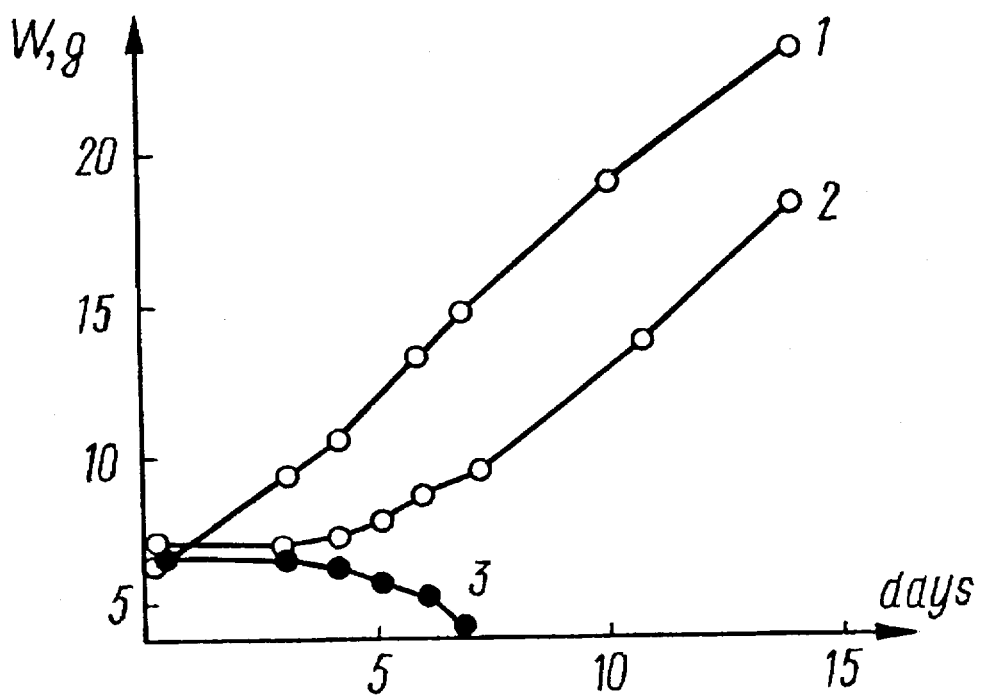

A criterion of the therapeutic effect was also the weight gain of the animals which, as has been established, is indicative of their convalescence. FIG. 2 presents the dynamics of changes in the body weight of mice infected with influenza A/Aichi/2/68 virus. Mice, 20–30 animals per group, were infected with a virus dose of 50 $MLD_{50}$/mouse and treated in a chamber with aprotinin aerosol by the standard method. In the course of the infection body weights were determined and mean values (in g) were put on the ordinate, while on the abscissa were days after infection.

Curve 1—weight of uninfected mice, curve 2—weight of infected mice treated with aprotinin, curve 3—weight of control infected mice treated with a gas-water mixture without aprotinin.

As will be seen in FIG. 2, in normal mice (uninfected) the gain in weight was approximately 1 g/day. In the group of mice infected with a lethal dose of influenza A/Aichi/2/68 virus the weight remained unchanged and then began to decrease which was associated with the animal' deaths. In the group of the aerosol-treated animals, early in the infection the weight gain was low, but from the 5th day postinfection the gain was about 1 g/day indicating the convalescence of the animals. A similar pattern of weight changes in the control and aerosol-treated mice was observed in the animals infected with Sendai virus. Thus, the application of aprotinin aerosol for animals suffering from the respiratory tract infection exerted a positive therapeutic effect manifested in rapid normalization of the body weight gain.

In the final stage of the work, the protective effect of aprotinin aerosol was evaluated in the experiments with a lethal dose of influenza A/Aichi/2/68 and B/HK/72 viruses or Sendai/960 virus. One should bear in mind that influenza B/HK/72 virus is less lethal for mice than the other two viruses.

Figure 3A:
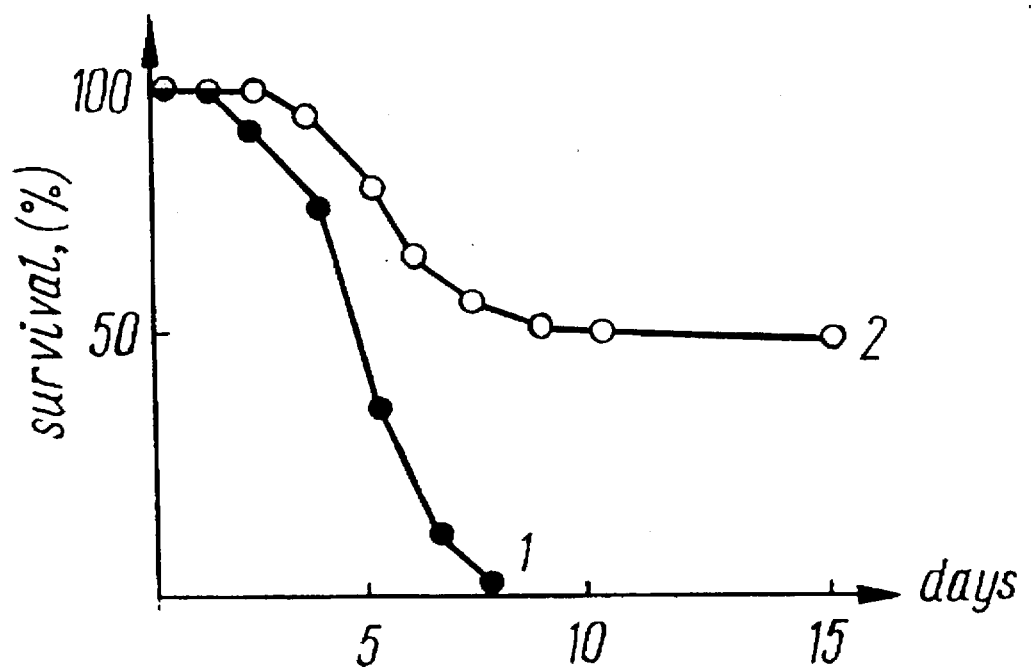
Figure 3B:
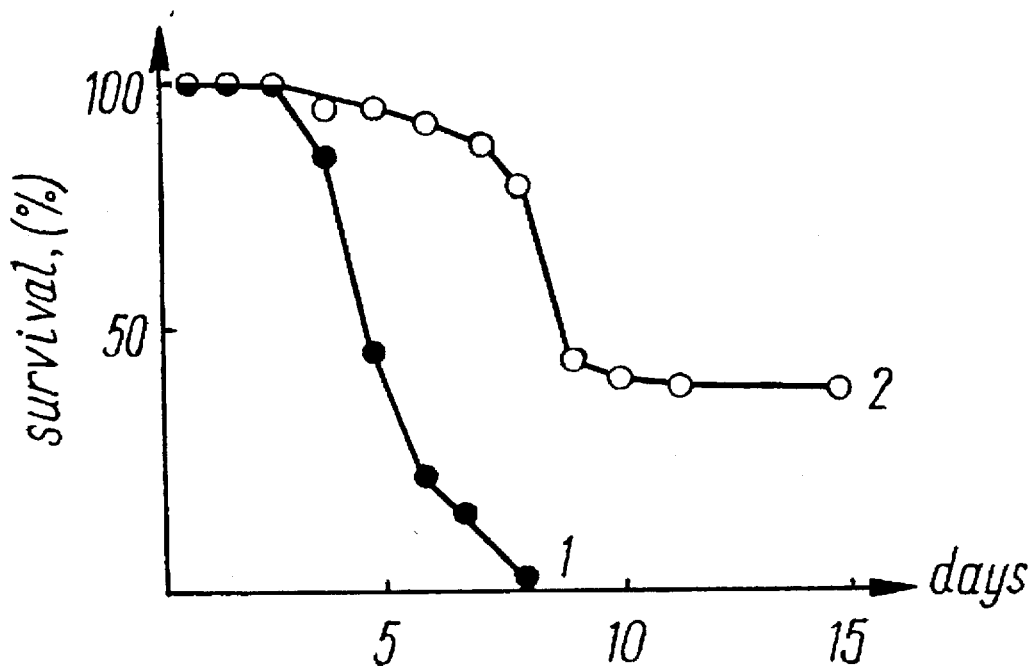

FIGS. 3a, b, c, d shows the protective effect of aprotinin aerosol in mice infected with the said viruses. The mice were infected with A/Aichi/2/68 virus (a, c), Sendai/960 virus (b) and B/HK/72 virus (d) at a multiplicity of 1 (d) or 50 (a, b, c) $MLD_{50}$/mouse, and then for 6.5 days were given a course of aprotinin aerosol inhalations (a, b, d) or intraperitoneal injections (c) by the schedule described above. In the course of infection the survival rate of the animals was recorded. In the ordinate—number of surviving mice (the cumulative percent), on the abcissa—days after infection. Curve 1—control infected but untreated mice, curve 2—mice treated with aprotinin aerosol.

Figure 3C:
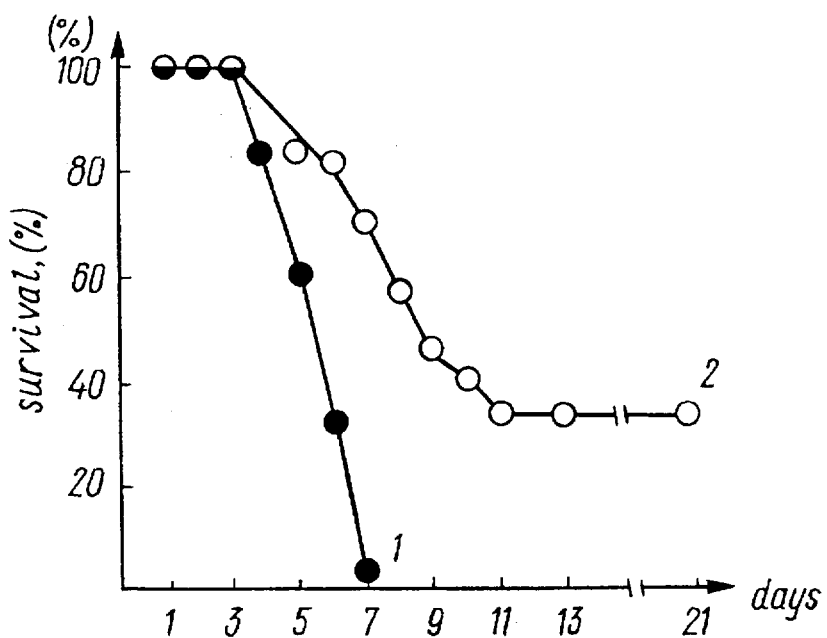
Figure 3D:
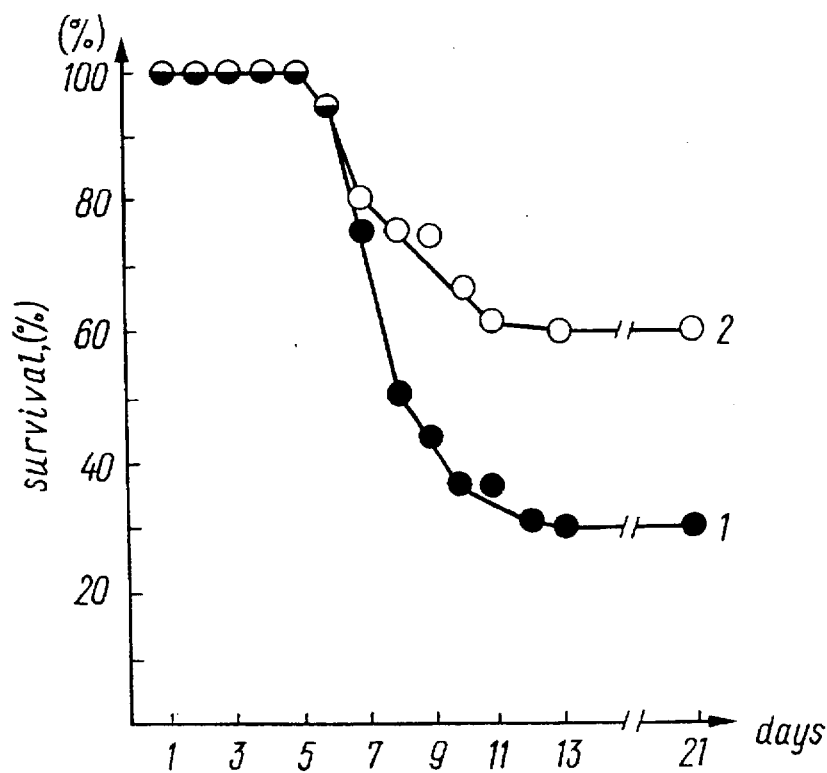

FIG. 3d shows that aprotinin aerosol protected from death 50% of mice infected with 1 $MLD_{50}$ of B/HK/72 virus. Since with the infecting doses of 1 to 10 $MLD_{50}$ of influenza A and Sendai viruses, both methods of treatment (parenteral injections and inhalations of aprotinin aerosol) gave approximately 90% to 100% protection, massive infecting doses were used for comparison of these methods of treatment: approximately 50 to 100 $MLD_{50}$/mouse. It will be seen in FIG. 3 (a, b), in the group of untreated animals 100% lethality was observed within 5–7 days in influenza (panel a) and within 6–8 days in paramyxovirus infection (b). In the treated animals, deaths started from 1 to 4 days later than in the control mice, and the protective effect was about 40% to 50%. In a parallel group of mice treated by intraperitoneal injections of aprotinin (15,000 KIU/mouse/day, 5–6 injections daily for 7 days) the protective effect was 30% as seen in FIG. 3c. The results of this series of experiments gave final confirmation to the conclusion of high therapeutic efficacy of application of low doses of aprotinin aerosol.

To evaluate the prophylactive effect of aprotinin aerosol, the experiments were carried out in uninfected mice (10 animals) to which two mice infected with influenza A/Aichi/2/68 virus at a multiplicity of about 0.1 $MLD_{50}$/mouse were placed in the same cage. Such groups of 12 animals were exposed to the gas-water mixture and aprotinin aerosol for 6–7 days, 3–4 exposures daily for 30–60 min each. On the 8th day mouse lungs were examined. In the control group given the mixture without aprotinin, inflammation foci were detected in the lungs and in a number of cases virus could be detected in the lungs. In the animals treated with the aerosol, no virus or inflammation foci could be detected. Thus, in the group the prophylactic effect of aprotinin aerosol was observed with inhibition of virus transmission from sick mice to normal ones.

Additionally, in experiments using an aqueous solution of aprotinin prepared as in Example 1, the influence of surfactants, in particular, Twin-80, glycerol, on the therapeutic efficacy in mice with influenza bronchopneumonia was studied, and the results are presented in the Table.

| Aprotinin aqueous solution | Therapeutic effect of aerosol (% of protection of mice) |
|---|---|
| 1. Without surfactant | 48 |
| 2. 0.3 vol. % Twin-80 | 60 |
| 3. 0.2 vol. % glycerol | 56 |

As will be seen in the Table, introduction of surfactants into the aerosol composition increased the protective effect of the aerosol by 10%-20%.

The compressed powder aerosol prepared as in Example 2 was tested in experimentally infected mice incubated in the exposure chamber as described above for using aqueous aerosol composition. In this series of the experiments it was found that the protective effect of the dry aprotinin aerosol with particle size of from 0.5 to 100 μm was about 40%-60% for influenza A and Sendai viruses.

The initial clinical trials carried out during an influenza outbreak caused by influenza type H3N2 virus demonstrated the therapeutic efficacy by aprotinin aerosol (Gordox preparation) administered by inhalation through a face mask or head chamber to the children with influenza. A shortening of the antigen-carrier period was observed: in untreated patients, viral antigens could be detected in the nasopharynx for approximately 6 days, and in the patients treated with aprotinin aerosol for up to 3 days. This indicates an earlier elimination of the virus from the body. The application of aprotinin aerosol shortened the persistence of the disease symptoms coryzs, coughing, catarrh of the upper respiratory tract) by 2-3 days and prevented the development of secondary complications.

Fields of application

The pharmaceutical aerosol composition on the basis of aprotinins, derivatives thereof, or aprotinin-like substances may find largescale application in medicine and veterinary as a therapeutic and prophylactic drug against a large group of viruses (influenza, parainfluenza, pneumoviruses, measles, mumps, respiratory-syncytial virus, coronaviruses, rhonoviruses, adenoviruses), the causative agents of many diseases of human and animal respiratory tract.

We claim:

1. A method for treatment and prevention of respiratory pathology of viral or viral-bacterial origin using an aerosol composition containing as active ingredient an inhibitor of proteases selected from the group consisting of aprotinins and derivatives thereof, said active ingredient being dissolved in water to form a solution, said method comprising inhalation or direct application of a therapeutically effective amount of the aerosol on the respiratory tract.

2. A method for treatment and prevention of respiratory pathology of viral or viral-bacterial origin using an aerosol composition containing as the active ingredient solid micronized particles of a proteinase inhibitor selected from the group consisting of aprotinins and derivatives thereof, the average particle size being in the range of from 0.5 to 20 μm, comprising inhalation or direct application of a therapeutically effective amount of the aerosol on the respiratory tract.

* * * * *